United States Patent
Feuerherm et al.

(10) Patent No.: US 9,682,930 B2
(45) Date of Patent: Jun. 20, 2017

(54) RHEUMATOID ARTHRITIS TREATMENT

(71) Applicant: Avexxin AS, Trondheim (NO)

(72) Inventors: Astrid Jullumstro Feuerherm, Trondheim (NO); Berit Johansen, Trondheim (NO)

(73) Assignee: Avexxin AS, Trondheim (NO)

( * ) Notice: Subject to any disclaimer, the term of this patent is extended or adjusted under 35 U.S.C. 154(b) by 0 days.

(21) Appl. No.: 13/783,088

(22) Filed: Mar. 1, 2013

(65) Prior Publication Data

US 2013/0245127 A1 Sep. 19, 2013

Related U.S. Application Data

(63) Continuation-in-part of application No. PCT/EP2011/065123, filed on Sep. 1, 2011.

(30) Foreign Application Priority Data

Sep. 1, 2011 (GB) .................................. 1014633.0

(51) Int. Cl.
*C07C 323/22* (2006.01)
*A61K 31/121* (2006.01)
*A61K 31/131* (2006.01)

(52) U.S. Cl.
CPC .......... *C07C 323/22* (2013.01); *A61K 31/121* (2013.01); *A61K 31/131* (2013.01)

(58) Field of Classification Search
CPC ........ C07C 323/22; A61K 31/121; A61K 3/10
See application file for complete search history.

(56) References Cited

U.S. PATENT DOCUMENTS

| | | | |
|---|---|---|---|
| 4,670,465 A | 6/1987 | Guzman et al. | |
| 6,255,496 B1 | 7/2001 | Banville et al. | |
| 6,688,468 B2 | 2/2004 | Waterman | |
| 7,101,875 B2 * | 9/2006 | McKew et al. | 514/228.2 |
| 7,687,543 B2 | 3/2010 | Johansen et al. | |
| 2005/0256141 A1 | 11/2005 | Nakagawa et al. | |
| 2006/0162240 A1 | 7/2006 | Filippini et al. | |
| 2009/0192201 A1 | 7/2009 | Selman-Housein Sosa | |

FOREIGN PATENT DOCUMENTS

| | | |
|---|---|---|
| EP | 0765661 A2 | 4/1997 |
| EP | 2147910 A1 | 1/2010 |
| JP | 09268153 A | 10/1997 |
| WO | 9738688 A1 | 10/1997 |
| WO | 9942101 A1 | 8/1999 |
| WO | 0002561 A1 | 1/2000 |
| WO | 2000034348 A1 | 6/2000 |
| WO | 01/05761 A1 | 1/2001 |
| WO | 2002060535 A1 | 8/2002 |
| WO | 03063878 A1 | 8/2003 |
| WO | 2006096579 A1 | 9/2006 |
| WO | 2006106438 A2 | 10/2006 |
| WO | 2008075366 A2 | 6/2008 |
| WO | 2008075978 A2 | 6/2008 |
| WO | 2009038671 A2 | 3/2009 |
| WO | 2009061208 A1 | 5/2009 |
| WO | 2010128401 A1 | 11/2010 |
| WO | 2010139482 A1 | 12/2010 |
| WO | 2011097276 A1 | 8/2011 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*
Sheridan, R.P. "Common Chemical Replacements in Drug-Like Compounds" J. Chem. Inf. Comput. Sci, 2002, vol. 42, pp. 103-108.*
European Office Action for corresponding European Application No. 11757227.1; dated Mar. 19, 2014, 8 pages.
Lamothe, Jennifer, et al., Efficacy of Giripladib, a Novel Inhibitor of Cytosolic Phospholipase A2a, in Two Different Mouse Models of Rheumatoid Arthritis, doi:10:1016/j. clim.2008.03.249, pp. 589-590.
Tai, Nobuyuki et al., Cytosolic phospholipase A2 alpha inhibitor, pyrroxyphene, displays anti-arthritic and anti-bone destructive action in a murine arthritis model; Inflammation Research (2010) 59:53-62.
www.everydayscience.com/chemistry/glossary/e.php (accessed Jul. 9, 2008).
Miller et al., Dietary Supplementation with Ethyl Ester Concentrations of Fish Oil (n-3) and Borage Oil (n-6) Polyunsaturated Fatty Acids, Induces Epidermal Generation of Local Putative Anti-Inflammatory Metabolites, Journal of Investigative Dermatology, 1991, 96(1), 98-103.
Machine Translation of JP 11199493 A.
Thommesen, L. et al; "Selective Inhibitors of Cytosolic or Secretory Phospholipase A2 Block TNF-Induced Activation of Transcription of Factor Nuclear Factor-kappaB and Expression of ICAM-1", The Journal of Immunology, vol. 161, 1998, pp. 3421-3430.
Flock, S. et al.; "Syntheses of Some Polyunsaturated Sulfur- and Oxygen-containing Fatty Acids Related to Eicosapentaenoic and Docosahexaenoic Acids", Acta Chemica Scandinavia, vol. 53, 1999, pp. 436-445.
Andersen, S. et al., "Elevated Expression of Human Nonpancreatic Phospholipase A2 in Psoriatic Tissue", Inflammation, vol. 18, No. 1, 1994.

(Continued)

*Primary Examiner* — Kendra D Carter
(74) *Attorney, Agent, or Firm* — Mintz Levin Cohn Ferris Glovsky and Popeo, P.C.; Peter F. Corless

(57) ABSTRACT

A compound of formula (I)

$$R\text{-}L\text{-}CO\text{-}X \qquad (I)$$

(wherein R is a $C_{10\text{-}24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;
L is a linking group forming a bridge of 1 to 5 atoms between the R group and the carbonyl CO; and
X is an electron withdrawing group)
for use in the treatment of rheumatoid arthritis.

8 Claims, 7 Drawing Sheets

(56) References Cited

OTHER PUBLICATIONS

Johansen, B. et al., "Phospholipase A2 in Psoriasis", Uhl W. Nevalainen, Buchler MW (eds): Phospholipase A2 Basic and Clinical Aspects in Inflammatory Diseases. Prog Surg. Basel, Karger, 1997, vol. 24, pp. 225-231.
Six, D. et al., "The Expanding Super-Family of Phospholipase A2 Enzymes: Classification and Characterization", Biochimica et Biophysica Acta 1488 (2000) 1-19.
Anthonsen, M. et al., "Functional Coupling Between Secretory and Cytosolic Phospholipase A2 Modulates Tumor Necrosis Factor-Alpha- and Interleukin-1Beta- Induced NF-Kb Activation", The Journal of Biological Chemistry, vol. 276, No. 32, issue of Aug. 10, pp. 30527-30536, 2001.
Sjursen, W., et al., "Secretory and Cytosolic Phospholipase A2 Regulate the Long-Term Cytokine-induced Eicosanoid Production in Human Keratinocytes", Cytokine, vol. 12, No. 8 Aug. 2000, pp. 1189-1194.
Sundler, R. et al., "Acyl-Chain Selectivity of the 85 Kda Phospholipase A2 and of the Release Process in Intact Macrophages", Biochem, J. (1994) 301, 455-458.
Aldamiz-Echevarria et al., Effect of docosahexaenoic acid administration on plasma lipid profile and metabolic parameters of children with methylmalonic acidaemia, J. Inherit Metab Dis, 2006, 29, 58-63.
www.webmd.com/skin-problems-and-treatments/psoriasis-overview (accessed Sep. 18, 2007).
Sandri, J. et al., Synthesis of all-(Z)-5, 8, 11, 14, 17—Eicosapentaenoic Acid and all-(Z)-4, 7, 10, 13, 16, 19-Docosahexaenoic Acid from (Z)-1, 1, 6, 6-Tetraisopropoxy-2-hexene, J. Org. Chem 1995, 60, 6627-6630.
Atkins (Lancet (2005) 365:1797-1806).
Cybulsky et al, The Journal of Biological Chemistry, 2002, 277:41342-41351.
Kishida, et al., Biochimica et Biophysica Acta, 1998, 1391:401-408.
Lianos, E.A., "Biosynthesis and role of arachidonic acid metabolites in glomerulonephritis", Nepron. 1984; 37(2): 73-78.
Cattell, V., "Nitric oxide and glomerulonephritis", Kidney Int. Mar. 2002, 61(3):816-21.
Couser, W.G., "Pathogenesis of glomerular damage in glomerulonephritis", Nephrol Dial Transplant. 1998:13 Suppl 1:10-5.
Kurogi, Y., "Mesangial cell proliferation inhibitors for the treatment of proliferative glomerular disease", Med Res Rev. Jan. 2003;23(1):15-31.
Papanikolaou, N., "Alteration of mercuric chloride-induced autoimmune glomerulonephritis in brown-Norway rats by herring oil, evening primrose oil and OKY-046 a selective TXA-synthetase inhibitor", Prostaglandins Leukot Med. May 1987;27(2-3): 129-49.
Shi, Y. et al., "Attenuation of mycotoxin-induced IgA nephropathy by eicosapentaenoic acid in the mouse: dose response and relation to IL-6 expression", J Nutr Biochem. Oct. 2006;17(10):697-706. Epub Jan. 9, 2006.
Larsen, L., et al., "Polyunsaturated thia- and oxa-fatty acids: incorporation into cell-lipids and their effects on arachidonic acid- and eicosanoid synthesis", Biochim Biophys Acta. Oct. 18, 1997;1348(3):346-54.
Albrightonson, L. et al.: "Selective inhibition of 5-lipoxygenase attenuates glomerulonephritis in the rat", Kidney Int. May 1994;45(5):1301-10.
Hansen, T., et al., "Syntheses of two cytotoxic polyunsaturated pyrrole metabolites of the marine sponge mycale micracanthoxea" Tetrahedron Leters 2006 45:2809-11.
Katagiri, T., et al., "Trifluoromethylated amino alcohol as chiral auxiliary for highly diastereoselective and fast Simmons-Smith cyclopropanation of allylic amine", 2006 Tetrahedron 17:1157-60.
Brown, et al., Protection of Oxygen-Sensitive Pharmaceuticals with Nitrogen, Journal of Pharmaceutical Sciences, 58 (2), 1969, 242-245.
Atsumi et al., "Distinct Roles of Two Intracellular Phospholipase A2s in Fatty Acid Release in the Cell Death Pathway," Journal of Biological Chemistry (2000), 275(24):18248-18258.
International Search Report issued in International Application No. PCT/EP2010/003384, Aug. 6, 2010, 5 pages.
Written Opinion issued in International Application No. PCT/EP2010/003384, Aug. 6, 2010, 7 pages.
J.C. McKew et al. "Indole Cytosolic Phospholipase A2 Inhibitors: Discovery and in Vitro and in Vivo Characterization of 4-{3-[5-Chloro-2-(2-{[(3,4-dichlorobenzyl)sulfonyl]amino}ethyl)-1-(diphenylmethyl)-1H-indol-3-yl]propyl}benzoic Acid, Efipladib" ) Journal of Medical Chemistry, 2008, vol. 51, No. 12 (pp. 3388-3413).
D.A. Six, et al. "Structure-Activity Relationship of 2-Oxoamide Inhibition of Group IVA Cytosolic Phospholipase A2 and Group V Secreted Phospholipase A2" Journal of Medicinal Chemistry, 2007, vol. 50, No. 17 (pp. 4222-4235).
International Search Report for PCT/EP2011/065123, Dec. 23, 2011 (5 pages).
Written Opinion for PCT/EP2011/065123, Dec. 23, 2011 (11 pages).
Huber, L.C., et al., Synovial fibroblasts: key players in rheumatoid arthritis; Rheumatology 2006; 45:669-675, Advance Access publication Mar. 27, 2006.
Kusunoki, Nasuko, et al.; Pro-apoptotic effect of nonsteroidal anti-inflammatory drugs on synovial fibroblast; Mod Rheumatol, DOI 10.007/s10165-008-012-8.
Flock S., et al.: Syntheses of some sulfur-containing polyunsaturated fatty acids as potential lipoxygenase inhibitors, Synthetic Communications, Taylor & Francis Group, Philadelphia, PA, vol. 37, No. 22, Jan. 1, 2007, pp. 4005-4015.
Ringbom, T., et al.: Cox-2 Inhibitory Effects of Naturally Occurring and Modified Fatty Acids, Journal of Natural Products, American Chemical Society, US, vol. 64, No. 6, Jan. 1, 2001, pp. 745-749.
Costabile, M. et al.; The Immunomodulatory Effects of Novel .beta.-Oxa, .beta.-Thia, and .gamma. -Thia Polyunsaturated Fatty Acids on Human T Lymphocyte Proliferation, Cytokine Production, and Activation of Protein Kinase C and MAPKs, Journal of Immunology, American Association of Immunologists, US, vol. 174, No. 1, Jan. 1, 2005, pp. 233-243.
Holmeide A. K., et al.; Syntheses of some polyunsaturated trifluoromethyl ketones as potential phospholipase A2 inhibitors, Journal of the Chemical Society, Perkin Transactions 1, Chemical Society, Letchworth; GB, Jan. 1, 2000, pp. 2271-2276.

\* cited by examiner

RHEUMATOID ARTHRITIS TREATMENT

CROSS-REFERENCE TO RELATED APPLICATIONS

The present application is a continuation-in-part of PCT/EP2011/065123 (WO2012/028688), entitled "Rheumatoid Arthritis Treatment Using Polyunsaturated Long Chain Ketones," which application claims the benefit of and priority to GB 1014633.0, filed Sep. 2, 2010. The disclosures of the PCT/EP011/065123 and GB 1014633.0 applications are each incorporated herein by reference in their entirety.

This invention relates to the use of certain polyunsaturated long-chain ketones for the treatment of rheumatoid arthritis and other chronic autoimmune diseases and in particular to ketones carrying electron withdrawing substituents alpha to the carbonyl functionality in such treatment.

The present inventors seek new treatments for rheumatoid arthritis (RA) and related conditions. Rheumatoid arthritis (RA) is an acquired, chronic, systemic, inflammatory disease that primarily affects the synovial membranes of multiple joints in the body. In RA, the immune system mistakenly attacks the synovium, and the following chronic inflammation causes joint pain, stiffness, swelling and loss of joint function by cartilage and bone destruction. Rheumatoid arthritis affects more than two million people in the United States alone. The interplay of genetics, immunogenic and environmental factors triggering RA is not completely understood and the triggering arthritogenic antigen is not yet identified. Regardless of the origin, the antigen activates CD4+ T-helper cells, which produce cytokines capable of activating a variety of cells within the joint, fuelling inflammation and degradation.

Once the synovitis is established, autocrine and paracrine signalling networks by cytokines and other inflammatory mediators such as eicosanoids contribute to disease perpetuation and joint destruction.

The inflammatory cytokines TNF and interleukin-1B (IL-1B) are implicated in the destruction of both articular cartilage and bone in RA. In early RA, the chronic synovitis results in soft tissue swelling due to edema, synovial cell hyperplasia and proliferation as well as infiltrates of immunoactive cells. As the synovitis progresses, inflammatory tissue mass expands to the articular surface, forming a pannus at the synovium and cartilage or subchondral bone interface. From this pannus, neutrophils and synoviocytes penetrate the cartilage or bone surfaces, leading to the maturation and activation of osteoclasts and chondrocytes. Activated synoviocytes directly contribute to joint destruction by secretion of various proteinases including matrix metalloproteinases (MMPs) and by inducing a chondrocyte phenotypic shift from anabolic to catabolic state, leading to loss and destruction of cartilage. As RA progresses, articular cartilage and bone subjacent to the pannus are degraded. Eventually the pannus fills the joint space, resulting in fibrosis, calcification and at last permanent ankylosis.

Inflammation therefore plays a significant role in RA pathology. Prostaglandin E2 (PGE2) is strongly elevated in RA and the beneficial anti-inflammatory and nociceptive effects of reducing PGE2 synthesis are well recognized. Early and intermediate molecular mediators of inflammation include tumour necrosis factor alpha (TNF-α), interleukins IL-1, IL-6, IL-8 and IL-15, transforming growth factor beta, fibroblast growth factor and platelet-derived growth factor. Once the inflammatory reaction is established, the synovium thickens, the cartilage and the underlying bone begins to disintegrate and evidence of joint destruction accrues.

Synovial fibroblasts are also key cells in the proliferation of RA. These cells appear to be in the centre of the local pathogenic events. Once activated, rheumatoid arthritis synovial fibroblasts produce a variety of cytokines, chemokines, and matrix-degrading enzymes that mediate the interaction with neighbouring inflammatory and endothelial cells. These interactions result in excessive growth of the cells in the synovia (synovial hyperplasia), which results in the progressive destruction of cartilage and bone.

There is no known cure for rheumatoid arthritis, but many types of treatment can alleviate symptoms and/or modify the disease process. The goal of treatment is two-fold: alleviating the current symptoms and preventing further deterioration of the joints. Typically, the latter goal is achieved with a disease modifying anti-rheumatic drug (DMARD), which can be supplemented with other medications such as anti-inflammatory or pain relief medications.

Non-steroidal anti-inflammatory drugs (NSAIDs) have long been used for the treatment of RA. NSAIDs reduce pain, fever and, in higher doses, inflammation. The mechanism of action of NSAIDs generally involves the inhibition of cyclooxegenase (COX) at sites of inflammation. Thus, NSAIDs were not generally considered to have an anti-rheumatic effect when used to treat RA. However, certain NSAIDs, such as celecoxib, have been reported to inhibit synovial hyperplasia by inducing apoptosis of the synovial fibroblasts.

Apart from NSAIDS and DMARD, the most successful therapeutic for RA patients are TNF-neutralising antibodies. However, biologics (e.g., monoclonal antibodies to TNF and IL-6 receptor, and recombinant soluble TNF receptor, etc.) may have adverse side effects, including reduced resistance towards infections, cancer development and immunity toward the biologic therapeutic itself.

As is clear from the discussion above, the pathology of arthritis is complex and many markers are implicated in the disease. Inflammation however, like many other diseases, plays an important role in the condition. The present inventors sought alternative therapies for RA not relying on NSAIDS or other known treatments.

The present inventors have realised that the compounds claimed herein have potential in the treatment of chronic inflammatory diseases in general and rheumatoid arthritis in particular. The inventors have found that a certain class of compounds based upon long chain unsaturated fatty acid molecules are useful in the treatment of rheumatoid arthritis. We show in the examples that the compounds of the invention have a variety of beneficial properties e.g. in relation to inflammatory markers PGE2, COX2 and IL-8. It was the appreciation that inhibition of these markers could lead to benefits in rheumatoid arthritis care that led to the invention.

The present inventors have realised that these compounds and others have utility also in the treatment of rheumatoid arthritis or other chronic inflammatory diseases.

SUMMARY OF INVENTION

Thus, viewed from one aspect the invention a compound of formula (I)

$$R\text{-}L\text{-}CO\text{---}X \qquad (I)$$

(wherein R is a $C_{10\text{-}24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;

L is a linking group forming a bridge of 1 to 5 atoms between the R group and the carbonyl CO; and X is an electron withdrawing group);

for use in the treatment of rheumatoid arthritis.

The invention also provides a series of new compounds. Viewed from another aspect the invention provides a compound of formula (II)

R-L1-CO—X    (II)

(wherein R and X are as hereinbefore defined;

L1 is a linking group forming a bridge of 1 to 5 atoms between the R group and the carbonyl CO, the atoms forming the backbone of said linking group being selected from carbon and/or the heteroatoms N, O, S, SO, $SO_2$;

wherein the linking group L1 comprises a ring within the backbone or is linear and the backbone atoms of the linking group are substituted with at least one side chain (in addition to any oxo group of SO or $SO_2$).

Viewed from another aspect the invention provides a method of treating rheumatoid arthritis comprising administering to an animal, preferably a mammal, e.g. human, an effective amount of a compound of formula (I) or (II) as hereinbefore described.

Viewed from another aspect the invention provides use of a compound of formula (I) or (II) as hereinbefore described for use in the manufacture of a medicament for treating rheumatoid arthritis.

The compounds of the invention are also envisaged as being useful in the treatment of chronic inflammatory diseases in general, preferably an autoimmune disease with type III hypersensitivity. In particular, the compounds may be used to treat chronic inflammatory disorders or diseases of the synovium. Thus, viewed from another aspect the invention a compound of formula (I)

R—CO—X    (I)

(wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds; and X is an electron withdrawing group)

for use in the treatment of a chronic autoimmune disease, preferably an autoimmune disease with type III hypersensitivity or a chronic inflammatory disorder or diseases of the synovium.

Viewed from another aspect the invention provides a method of treating an autoimmune disease, preferably an autoimmune disease with type III hypersensitivity, or a chronic inflammatory disorder or diseases of the synovium comprising administering to an animal, preferably a mammal, e.g. human, an effective amount of a compound of formula (I) or (II) as hereinbefore described.

Viewed from another aspect the invention provides use of a compound of formula (I) or (II) as hereinbefore described for use in the manufacture of a medicament for treating an autoimmune disease, preferably an autoimmune disease with type III hypersensitivity, or a chronic inflammatory disorder or diseases of the synovium.

DETAILED DESCRIPTION

This invention involves the use of compounds of formula (I) in the treatment of rheumatoid arthritis and related conditions as well as chronic inflammatory disorders and disorders of the synovium.

The group R preferably comprises 5 to 9 double bonds, preferably 5 or 8 double bonds, e.g. 5 to 7 double bonds such as 5 or 6 double bonds. These bonds should be non-conjugated. It is also preferred if the double bonds do not conjugate with the carbonyl functionality.

The double bonds present in the group R may be in the cis or trans configuration however, it is preferred if the majority of the double bonds present (i.e. at least 50%) are in the cis configuration. In further advantageous embodiments all the double bonds in the group R are in the cis configuration or all double bonds are in the cis configuration except the double bond nearest the carbonyl group which may be in the trans configuration.

The group R may have between 10 and 24 carbon atoms, preferably 12 to 20 carbon atoms, especially 17 to 19 carbon atoms.

Whilst the R group can be interrupted by at least one heteroatom or group of heteroatoms, this is not preferred and the R group backbone preferably contains only carbon atoms.

The R group may carry up to three substituents, e.g. selected from halo, $C_{1-6}$ alkyl e.g. methyl, $C_{1-6}$ alkoxy. If present the substituents are preferably non-polar, and small, e.g. a methyl group. It is preferred however, if the R group remains unsubstituted.

The R group is preferably linear. It preferably derives from a natural source such as a long chain fatty acid or ester. In particular, the R group may derive from AA, EHA or DHA.

L is a linking group forming a bridge of 1 to 5 atoms between the R group and the carbonyl CO. The linking group L provides a bridging group of 1 to 5 backbone atoms, preferably 2 to 4 backbone atoms between the R group and the carbonyl. The atoms in the backbone of the linker may be carbon and/or be heteroatoms such as N, O, S, SO, $SO_2$. The atoms can form part of a ring and the backbone atoms of the linking group can be substituted with side chains, e.g. with groups such as $C_{1-6}$ alkyl, oxo, alkoxy, or halo.

Preferred components of the linking group are —$CH_2$—, —CH($C_{1-6}$alkyl)-, —N($C_{1-6}$alkyl)-, —NH—, —S—, —O—, —CH═CH—, —CO—, —SO—, —$SO_2$— which can be combined with each other in any (chemically meaningful) order to form the linking group. Thus, by using two methylene groups and an —S— group the linker —$SCH_2CH_2$— is formed.

It is highly preferred if the linking group L contains at least one heteroatom in the backbone. It is also preferred if the first backbone atom of the linking group attached to the R group is a heteroatom or group of heteroatoms.

It is highly preferred if the linking group L contains at least one —$CH_2$— link in the backbone. Ideally the atoms of the linking group adjacent the carbonyl are —$CH_2$—.

It is preferred that the group R or the group L (depending on the size of the L group) provides a heteroatom or group of heteroatoms positioned α, β, γ, or δ to the carbonyl, preferably β or γ to the carbonyl. Preferably the heteroatom is O, N or S or a sulphur derivative such as SO.

Highly preferred linking groups therefore are —$NH_2CH_2$, —NH(Me)$CH_2$—, —$SCH_2$—, —$SOCH_2$—, —$COCH_2$—

It is also within the invention for the linking group to be a ring or to comprise a ring. Thus for example, the linker might be thiophene, e.g. 2,4-thiophene which provides a two atom bridge to the carbonyl (via the shortest route). It would also be possible for the linker to be a ring such as furan, tetrahydrofuran, piperidine, cyclohexane, benzene or pyridine. Where the linker comprises a ring it is preferred if this is a 5 or 6 membered ring. It is preferred if the ring comprises at least one heteroatom or group of heteroatoms. It is preferred if the ring is unsaturated or aromatic. When the R and COX groups bind directly to such a ring, it is preferred if the R group and COX group bind on different atoms and preferred if they bind on carbon atoms of the ring.

The substitution pattern is preferably such that the R and carbonyl substituents are alpha, gamma to each other (i.e. 1,3 or 2, 4 or 3,5-split).

For the avoidance of doubt, it is stressed that the 1 to 5 atom bridge should be counted as the shortest route from the start of the linker to the carbonyl.

Suitable ring linkers are shown below in connection with the discussion of L1.

It is also within the scope of the invention for the linker to comprise a ring and non ring portion, e.g. $CH_2$-thiophene or $NH_2$-thiophene and so on. In such a linker it is preferred if the R group binds directly to the ring and that the carbonyl group binds to the non ring portion, e.g. a —$CH_2$— linkage. The skilled man will be able to devise all kinds of different linkers suitable for use in the invention.

Highly preferred linking groups are —$CH_2$—, —$CH_2$—$CH_2$—, —CH(Me), —CH(Me)$CH_2$—, —CH(Me)-CH(Me)-, $SCH_2$, $NHCH_2$, N(Me)$CH_2$, 2,4-thiophene and 2,5-thiophene.

In compounds of formula (II), the linking group L1 is a linking group forming a bridge of 1 to 5 atoms between the R group and the carbonyl CO, the atoms forming the backbone of said linking group being selected from carbon and/or the heteroatoms N, O, S, SO, $SO_2$ wherein the linking group L1 comprises a ring within the backbone or is linear and the backbone atoms of the linking group are substituted with at least one side chain (in addition to any oxo group of SO or $SO_2$).

The linking group L1 preferably provides a backbone of 2 to 4 backbone atoms between the R group and the carbonyl.

Where the backbone is linear (i.e. it does not comprise a ring structure), at least one of the atoms in the backbone carries a side chain. That side chain is in addition to an oxo group that might be present on a SO or $SO_2$ group. Suitable side chains include $C_{1-6}$ alkyl, further oxo, alkoxy, $NH_2$, $N(C_{1-6}alkyl)H$, $N(C_{1-6}alkyl)_2$, or halo.

Such a side chain preferably binds to a heteroatom in the backbone of the linker L1. Preferably the backbone atoms adjacent the carbonyl group are not branched. Ideally there should be only one side chain present.

Preferred components of the linking group are —$CH_2$—, —CH($C_{1-6}$alkyl)-, —N($C_{1-6}$alkyl)-, —NH—, —S—, —O—, —CH=CH—, —CO—, —SO—, —$SO_2$— which can be combined with each other in any (chemically meaningful) order to form the linking group, bearing in mind the requirement for at least one side chain in the L1 group.

It is highly preferred if the linking group L1 contains at least one heteroatom in the backbone. It is also preferred if the first backbone atom of the linking group L1 attached to the R group is a heteroatom or group of heteroatoms.

It is highly preferred if the linking group L1 contains at least one —$CH_2$— link in the backbone. Ideally the atoms of the linking group adjacent the carbonyl are —$CH_2$—.

Highly preferred linear linking groups L1 are —NH(Me)$CH_2$—.

It is also within the invention for the linking group to be a ring or to comprise a ring. For the linking group to comprise a ring, the ring must actually be present as the linker or part of the linker as opposed to a side chain off the main linking atoms.

Thus for example, the linker might be thiophene, e.g. 2,4-thiophene which provides a two atom bridge to the carbonyl (via the shortest route). It would also be possible for the linker to be a ring such as furan, tetrahydrofuran, piperidine, cyclohexane, benzene or pyridine. Where the linker comprises a ring it is preferred if this is a 5 or 6 membered ring. It is preferred if the ring comprises at least one heteroatom or group of heteroatoms.

It is preferred if the ring is unsaturated or aromatic. When the R and COX groups bind directly to such a ring, it is preferred if the R group and COX group bind on different atoms, It is also preferred if they bind on carbon atoms of the ring.

The substitution pattern is preferably such that the R and carbonyl substituents are alpha, gamma to each other (i.e. 1,3 or 2,4 or 3,5-split). The number of atoms in the backbone of the linking group will be determined via the shortest route round the ring connected the R and CO parts of the molecule.

Suitable ring linkers are shown below where the R group and carbonyl can bind to any carbon atoms or available nitrogen atoms on these rings:

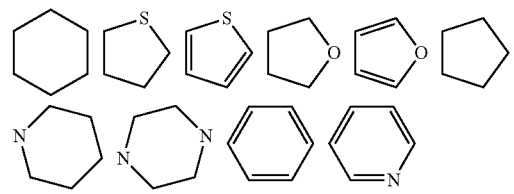

It is also within the scope of the invention for the linker to comprise a ring and non ring portion, e.g. $CH_2$-thiophene or $NH_2$-thiophene and so on. In such a linker it is preferred if the R group binds directly to the ring and that the carbonyl group binds to the non ring portion, e.g. a —$CH_2$— linkage. Where the linker contains a ring portion, it is not required that any non ring portion carries a side chain.

Highly preferred linking groups are L1 are —CH(Me), —CH(Me)$CH_2$—, —CH(Me)-CH(Me)-, N(Me)$CH_2$, 2,4-thiophene and 2,5-thiophene.

The group X is an electron withdrawing group. Suitable groups in this regard include O—$C_{1-6}$ alkyl, CN, $OCO_2$—$C_{1-6}$ alkyl, phenyl, $CHal_3$, $CHal_2H$, $CHalH_2$ wherein Hal represents a halogen, e. g. fluorine, chlorine, bromine or iodine, preferably fluorine. Especially, the electron withdrawing group is CN, phenyl, $CHal_3$, $CHal_2H$, $CHalH_2$ wherein Hal represents a halogen, e. g. fluorine, chlorine, bromine or iodine, preferably fluorine.

In a preferred embodiment the electron withdrawing group is $CHal_3$, especially $CF_3$.

Thus, viewed from another aspect the invention provides a compound of formula (III)

R—Y1-Y2-CO—X (III)

wherein R and X are as hereinbefore defined;

Y1 is selected from O, S, NH, N($C_{1-6}$-alkyl), SO or $SO_2$ and

Y2 is $(CH_2)_n$ or CH($C_{1-6}$ alkyl); or

Y1 and Y2 taken together form a 5 or 6 membered homo or heterocyclic, optionally unsaturated or aromatic ring; or Y1 forms a 5 or 6 membered homo or heterocyclic, optionally unsaturated or aromatic ring and Y2 is $(CH_2)n$;

where n is 1 to 3, preferably 1;

for use in the treatment of a condition discussed herein.

Highly preferred compounds for use in the invention are depicted below.

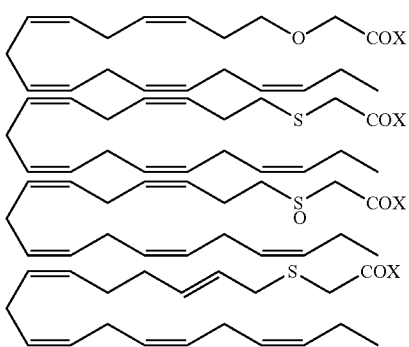

As noted above, certain compounds are new and form a further aspect of the invention.

Thus viewed from another aspect the invention provides a compound of formula (IV)

R—Y3-Y4-CO—X      (IV)

wherein R and X are as hereinbefore defined;
Y3 and Y4 taken together form a 5 or 6 membered homo or heterocyclic, saturated, unsaturated or aromatic ring; or
Y3 forms a 5 or 6 membered homo or heterocyclic, saturated, unsaturated or aromatic ring and Y4 is $(CH_2)n$;
where n is 1 to 3, preferably 1.

Further compounds which are new include a compound of formula (V)

$RN(C_{1-6}alkyl)(CH_2)_nCOX$      (V)

where R, n and X are as hereinbefore defined, especially the compound:

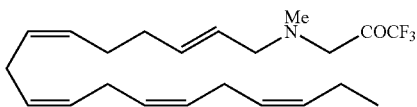

Further preferred compounds which are new are those in which the L1 group is a ring or comprises a ring.

Preferred compounds of formula (II) are depicted below.

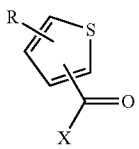      (VI)

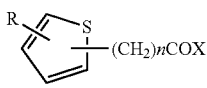      (VII)

where n is 1 to 3, e.g. 1 to 2.

Especially preferably the groups bind to the 2 and 4 positions of the ring (where atom 1 is the S atom).

Viewed from another aspect the invention provides a pharmaceutical composition comprising any new compound as hereinbefore defined in combination with at least one pharmaceutically acceptable excipient.

Where possible, the compounds of the invention can be administered in salt, solvate, prodrug or ester form, especially salt form. Preferably however, no such form is used.

Typically, a pharmaceutical acceptable salt may be readily prepared by using a desired acid. The salt may precipitate from solution and be collected by filtration or may be recovered by evaporation of the solvent. For example, an aqueous solution of an acid such as hydrochloric acid may be added to an aqueous suspension of a compound of formula (I) and the resulting mixture evaporated to dryness (lyophilised) to obtain the acid addition salt as a solid. Alternatively, a compound of formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulphonates (eg methanesulphonate, ethanesulphonate, benzenesulphonate or p-toluenesulphonate) and isethionate. Representative examples include trifluoroacetate and formate salts, for example the bis or tris trifluoroacetate salts and the mono or diformate salts, in particular the tris or bis trifluoroacetate salt and the monoformate salt.

Compounds of formula (I) may be manufactured using known chemical synthetic routes. It is convenient to begin synthesis from the commercially available compounds arachidonic acid (AA), EPA (all-Z-eicosa-5,8,11,14,17-pentaenoic acid) or DHA (all-Z-docosa-4,7,10,13,16,19-hexaenoic acid). Conversion of the acid functionality of these compounds into, for example a —$COCF_3$ group can be achieved readily, e.g. by converting the carboxylic acid into its corresponding acid chloride and reacting the same with trifluoroacetic anhydride in the presence of pyridine.

Introduction of a heteroatom into the carbon chain is also achieved readily. Conveniently, for example, the starting acid is reduced to an alcohol and, if required, converted to the corresponding thiol. The nucleophilic thiol may then be reacted with a group such as $BrCH_2COCF_3$ thereby introducing the carbonyl and electron withdrawing species. Complete synthetic protocols may be found in J. Chem. Soc., Perkin Trans 1, 2000, 2271-2276 or J. Immunol., 1998, 161, 3421.

Where the backbone of the molecule contains a nitrogen atom, an alternative synthesis is required. Formation of a polyunsaturated alcohol can be achieved using protocols give in the above Perkin Trans paper. Thereafter, conversion of an alcohol —OH to —$NH_2$ with, for example, phthalimide and subsequent hydrazine reduction allows formation of a —$NH_2CH_2COCF_3$ group by reaction with trifluoropropyleneoxide (TFPO) and oxidation of the hydroxyl to a ketone. This reaction is shown below.

Methylation of the nitrogen can be effected before this reaction by the formation of an N—BOC group and reduction, e.g. with lithium aluminium hydride. Reaction with TFPO and oxidation yields the linker NMe-$CH_2$.

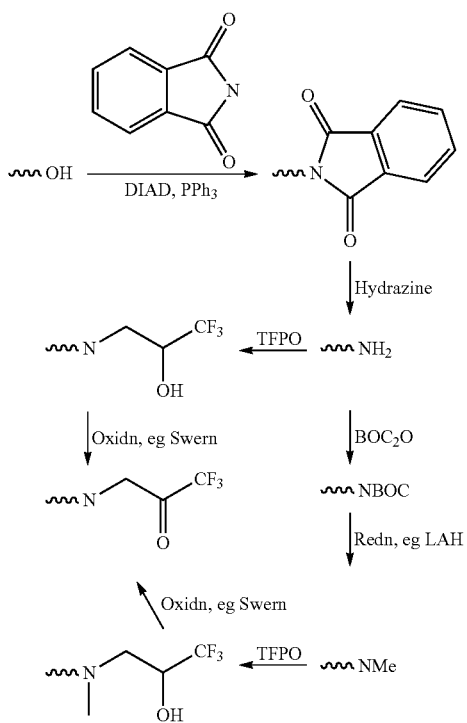

This forms a further aspect of the invention which therefore provides a process for the preparation of a compound of formula (I) comprising:
(I) converting the compound R—OH to R—NH$_2$,
(II) optionally methylating the N atom;
(III) reacting with TFPO; and
(IV) oxidising the formed hydroxyl to a ketone.

The compounds of the invention are proposed primarily for use in the treatment of, inter alia, rheumatoid arthritis.

By treating or treatment is meant at least one of:

(i). preventing or delaying the appearance of clinical symptoms of the disease developing in a mammal;

(ii). inhibiting the disease i.e. arresting, reducing or delaying the development of the disease or a relapse thereof or at least one clinical or subclinical symptom thereof, or (iii). relieving or attenuating one or more of the clinical or subclinical symptoms of the disease.

The benefit to a subject to be treated is either statistically significant or at least perceptible to the patient or to the physician. In general a skilled man can appreciate when "treatment" occurs.

The word "treatment" is also used herein to cover prophylactic treatment, i.e. treating subjects who are at risk of developing a disease in question.

The compounds of the invention can be used on any animal subject, in particular a mammal and more particularly to a human or an animal serving as a model for a disease (e.g., mouse, monkey, etc.).

In order to treat a disease an effective amount of the active agent needs to be administered to a patient. A "therapeutically effective amount" means the amount of a compound that, when administered to an animal for treating a state, disorder or condition, is sufficient to effect such treatment. The "therapeutically effective amount" will vary depending on the compound, the disease and its severity and the age, weight, physical condition and responsiveness of the subject to be treated and will be ultimately at the discretion of the attendant doctor.

While it is possible that, for use in the methods of the invention, a compound of formula I may be administered as the bulk substance, it is preferable to present the active ingredient in a pharmaceutical formulation, for example, wherein the agent is in admixture with a pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

It will be appreciated that pharmaceutical compositions for use in accordance with the present invention may be in the form of oral, parenteral, transdermal, inhalation, sublingual, topical, implant, nasal, or enterally administered (or other mucosally administered) suspensions, capsules or tablets, which may be formulated in conventional manner using one or more pharmaceutically acceptable carriers or excipients.

There may be different composition/formulation requirements depending on the different delivery systems. Likewise, if the composition comprises more than one active component, then those components may be administered by the same or different routes.

The pharmaceutical formulations of the present invention can be liquids that are suitable for oral, mucosal and/or parenteral administration, for example, drops, syrups, solutions, injectable solutions that are ready for use or are prepared by the dilution of a freeze-dried product but are preferably solid or semisolid as tablets, capsules, granules, powders, pellets, pessaries, suppositories, creams, salves, gels, ointments; or solutions, suspensions, emulsions, or other forms suitable for administration by the transdermal route or by inhalation.

The compounds of the invention can be administered for immediate-, delayed-, modified-, sustained-, pulsed- or controlled-release applications.

In one aspect, oral compositions are slow, delayed or positioned release (e.g., enteric especially colonic release) tablets or capsules. This release profile can be achieved without limitation by use of a coating resistant to conditions within the stomach but releasing the contents in the colon or other portion of the GI tract wherein a lesion or inflammation site has been identified or a delayed release can be achieved by a coating that is simply slow to disintegrate or the two (delayed and positioned release) profiles can be combined in a single formulation by choice of one or more appropriate coatings and other excipients. Such formulations constitute a further feature of the present invention.

Suitable compositions for delayed or positioned release and/or enteric coated oral formulations include tablet formulations film coated with materials that are water resistant, pH sensitive, digested or emulsified by intestinal juices or sloughed off at a slow but regular rate when moistened. Suitable coating materials include, but are not limited to, hydroxypropyl methylcellulose, ethyl celulose, cellulose acetate phthalate, polyvinyl acetate phthalate, hydroxypropyl methylcellulose phthalate, polymers of metacrylic acid and its esters, and combinations thereof. Plasticizers such as, but not limited to polyethylene glycol, dibutylphthalate, triacetin and castor oil may be used. A pigment may also be used to color the film. Suppositories are be prepared by using carriers like cocoa butter, suppository bases such as Suppocire C, and Suppocire NA50 (supplied by Gattefosse Deutschland GmbH, D-Weil am Rhein, Germany) and other Suppocire type excipients obtained by interesterification of hydrogenated palm oil and palm kernel oil (C8-C18 triglycerides), esterification of glycerol and specific fatty acids, or polyglycosylated glycerides, and whitepsol (hydrogenated plant oils derivatives with additives). Enemas are formulated by using the appropriate active compound according to the present invention and solvents or excipients for suspensions. Suspensions are produced by using micronized compounds, and appropriate vehicle containing suspension stabilizing agents, thickeners and emulsifiers like carboxymethylcellulose and salts thereof, polyacrylic acid and salts thereof, carboxyvinyl polymers and salts thereof, alginic acid and salts thereof, propylene glycol alginate, chitosan, hydroxypropylcellulose, hydroxypropylmethylcellulose, hydroxyethylcellulose, ethylcellulose, methylcellulose, polyvinyl alcohol, polyvinyl pyrrolidone, N-vinylacetamide polymer, polyvinyl methacrylate, polyethylene glycol, pluronic, gelatin, methyl vinyl ether-maleic anhydride copolymer, soluble starch, pullulan and a copolymer of methyl acrylate and 2-ethylhexyl acrylate lecithin, lecithin derivatives, propylene glycol fatty acid esters, glycerin fatty acid esters, sorbitan fatty acid esters, polyoxyethylene sorbitan fatty acid esters, polyethylene glycol fatty acid esters, polyoxyethylene hydrated caster oil, polyoxyethylene alkyl ethers, and pluronic and appropriate buffer system in pH range of 6.5 to 8. The use of preservatives, masking agents is suitable. The average diameter of micronized particles can be between 1 and 20 micrometers, or can be less than 1 micrometer. Compounds can also be incorporated in the formulation by using their water-soluble salt forms.

Aternatively, materials may be incorporated into the matrix of the tablet e.g. hydroxypropyl methylcellulose, ethyl cellulose or polymers of acrylic and metacrylic acid esters. These latter materials may also be applied to tablets by compression coating.

Pharmaceutical compositions can be prepared by mixing a therapeutically effective amount of the active substance with a pharmaceutically acceptable carrier that can have different forms, depending on the way of administration.

Pharmaceutical compositions can be prepared by using conventional pharmaceutical excipients and methods of preparation. The forms for oral administration can be capsules, powders or tablets where usual solid vehicles including lactose, starch, glucose, methylcellulose, magnesium stearate, di-calcium phosphate, mannitol may be added, as well as usual liquid oral excipients including, but not limited to, ethanol, glycerol, and water. All excipients may be mixed with disintegrating agents, solvents, granulating agents, moisturizers and binders. When a solid carrier is used for preparation of oral compositions preparation can be in the form of powder, capsules containing granules or coated particles, tablets, hard gelatin capsules, or granules without limitation, and the amount of the solid carrier can vary (between 1 mg to 1 g). Tablets and capsules are the preferred oral composition forms.

Examples of pharmaceutically acceptable disintegrants for oral compositions useful in the present invention include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and crosslinked polyvinylpyrrolidone.

Examples of pharmaceutically acceptable binders for oral compositions useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants useful in the compositions of the invention include, but are not limited to, magnesium stearate, talc, polyethylene glycol, polymers of ethylene oxide, sodium lauryl sulfate, magnesium lauryl sulfate, sodium oleate, sodium stearyl fumarate, and colloidal silicon dioxide.

Examples of suitable pharmaceutically acceptable odorants for the oral compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include, but are not limited to, synthetic and natural dyes such as titanium dioxide, beta-carotene and extracts of grapefruit peel.

Suitable examples of pharmaceutically acceptable sweeteners for the oral compositions include, but are not limited to, aspartame, saccharin, saccharin sodium, sodium cyclamate, xylitol, mannitol, sorbitol, lactose and sucrose. Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulfate and polysorbates.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetraacetic acid (EDTA), thiourea, tocopherol and butyl hydroxyanisole.

The pharmaceutical compositions of the invention may contain from 0.01 to 99% weight—per volume of the active material.

A therapeutically effective amount of the compound of the present invention can be determined by methods known in the art. The therapeutically effective quantities will depend on the age and on the general physiological condition of the patient, the route of administration and the pharmaceutical formulation used. The therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

It is advantageous if the medicament of the invention is taken orally or administered topically.

The compounds of the invention may be used in the treatment of rheumatoid arthritis and other chronic inflammatory diseases in general as well as diseases of the synovium and autoimmune conditions. In particular, the compounds of the invention may be used to treat Henoch-Schönlein purpura, Hypersensitivity vasculitis, Reactive arthritis, Farmer's lung, Serum sickness, Arthus reaction, Systemic lupus erythematosus, Subacute bacterial endocarditis as well as arthritis in general and osteoarthritis.

The compounds of the invention may be used to treat rheumatoid arthritis in combination with other known pharmaceuticals for said purpose and this forms a further aspect of the invention. Other useful pharmaceuticals include disease modifying anti-rheumatic drugs, anti-inflammatory agents such as glucocorticoids or non-steroidal anti-inflammatory drugs, analgesics, and pain relief medicaments.

The invention is described further below with reference-to the following non-limiting examples and figures.

EXAMPLES

Figure 1:
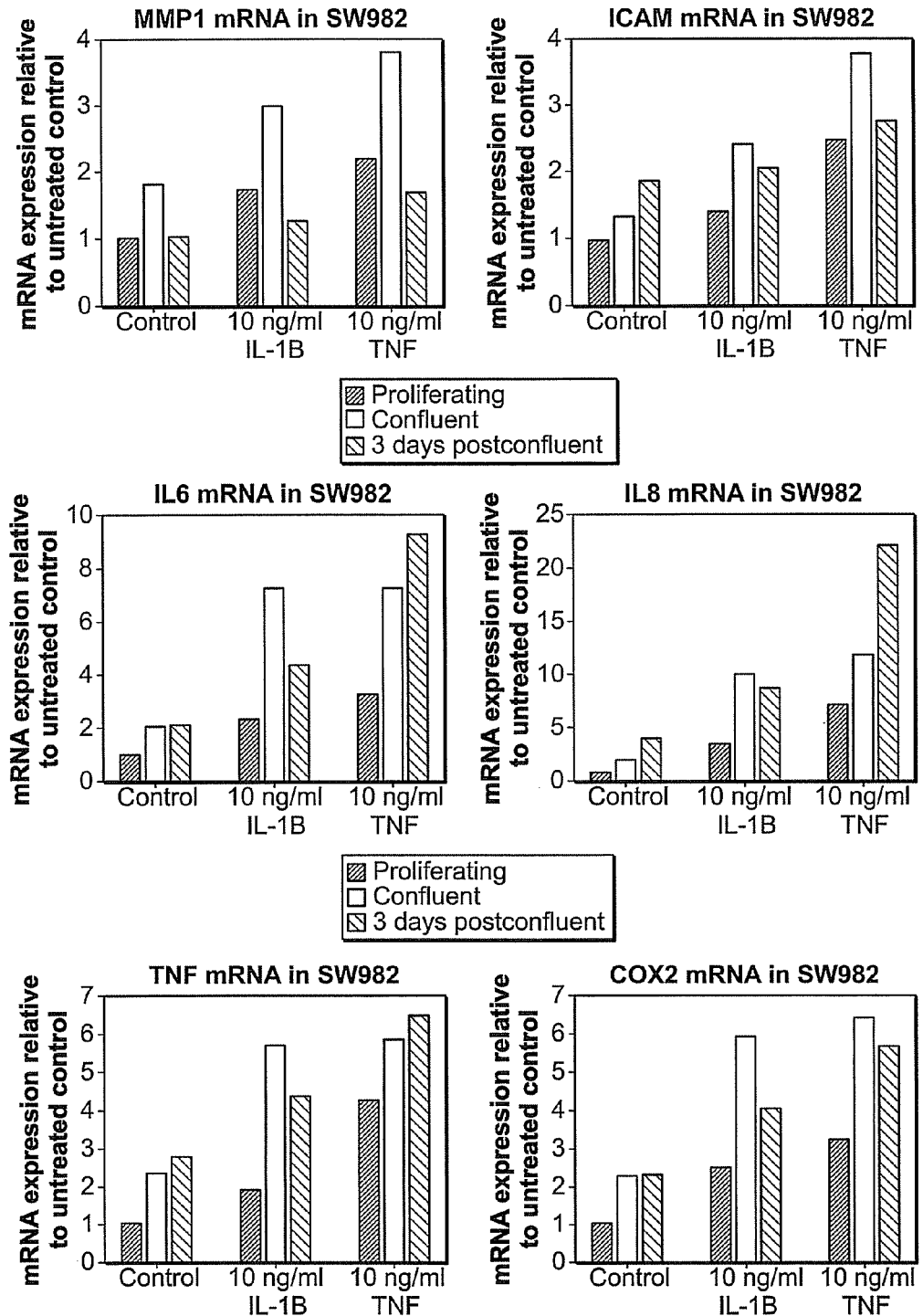
FIG. 1 shows qPCR determination of MMP1, ICAM, IL-6, IL-8, TNF and COX2 expression in proliferating, confluent and differentiated synoviocytes stimulated with the cytokines IL-1 and TNF.

The following compounds were used in the Experiments:

Compound 1

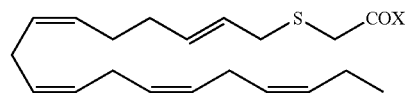

Compound 2

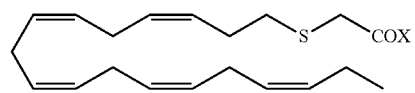

X=$CF_3$ in both compounds 1 and 2

These compounds were synthesised based on. Chem. Soc., Perkin Trans 1, 2000, 2271-2276.

Materials and Methods

Reagents

The Cell Culture SW982 model cell line at a confluent or spheroid state (Wada Y, 2005) was used since gene expression and generation of proinflammatory cytokines resemble RA-derived synovial fibroblast-like cells.

Stimulation

For stimulation experiments 0.5 mL of a cell suspension (5-7×105 cells/mL) were seeded inside the inner wells of 48-well plates. The outer wells were filled with 0.5 mL PBS. For nearly confluent populations, cells were incubated for one day (37° C., 5% CO2). In order to yield post-confluent cells, plates were left in the incubator for 3 days. After this incubation time, 300 μL of the supernatant was removed and replaced by 50 μL of stimulation medium.

Inhibition

Inhibition was performed in a similar manner as the stimulation. After seeding, incubation and replacement of the medium by 200 μL 0.5% FBS in DMEM, 50 μL of the particular inhibitor solution was added (Table 1). After 2 hours at 37° C., 50 μL of the supernatant was removed and replaced by the three stimulants described above.

TABLE 1

Concentrations of the different inhibitors.
Compound 2 and Compound 1 were diluted 1:50 in 96% ethanol
prior to the preparation of the 50 µM pre-dilutions
in DMEM/0.5% FBS.

SB203580 was directly
diluted in the medium.

| Inhibitor | Stock concentration | Final concentration |
|---|---|---|
| Compound 1 | 2M | 10 µM |
| Compound 2 | 2M | 10 µM |
| SB203580 | 10 mM | 10 µM |

PGE2 Analysis

PGE$_2$ Detection

Samples and controls were slowly thawed and diluted (between 1:1 and 1:2500) in the standard diluent. The maximal dilution was 1:10 for one step. That is why several intermediate dilutions were prepared. In the beginning all values were determined from duplicates. After having minimized technical errors, samples were only analyzed as individuals. All further steps, except for some minor corrections, were performed according to the manufacturer's recommendations as can be found in the manual of the EIA kit. In order to optimize the results, the incubation time of the alkaline phosphatase substrate was prolonged by 15 minutes. During the incubation, the plates were kept in the dark. An example of the arrangements of the samples and controls is illustrated in the appendix. The read-out was carried out with a Multiscan plate reader (Ascent Labsystems) at wavelengths of 414 and 595 nm after 10 seconds shaking at 120 rpm. The corresponding software to obtain the data was the Ascent software for Multiscan, Version 2.4.1.

Data were processed using Microsoft Office Excel 2003 and SigmaPlot 10.0.

Example 1 (Reference)

Effectiveness of TNF and IL1 as Inducers of Proinflammatory Mediators in Non-Proliferating SW982 Synoviocyte Cells The effectiveness of two cytokines, TNF and IL1 as inducers of proinflammatory mediators in proliferating, confluent and differentiated (three days post-confluent) SW982 cells was investigated (SW982 is a synoviocyte cell line, used throughout the examples of this application). Matrix metalloproteinase (MMP1), interstitial adhesion molecule (ICAM), IL6, IL8, TNF and the enzyme COX2 were assessed on transcriptional level by qPCR. The results are shown in FIG. 1. FIG. 1 shows a clear trend that TNF is a more powerful inducer compared to IL1; however, both cytokines are strong inducers for the range of proinflammatory mediators that were assessed. Therefore, the model systems used in the following examples have clinical relevance for the treatment of RA.

Example 2

Compound 2 is a Potent Inhibitor of Arachidonic Acid Release in SW982 Cells

Figure 1B:
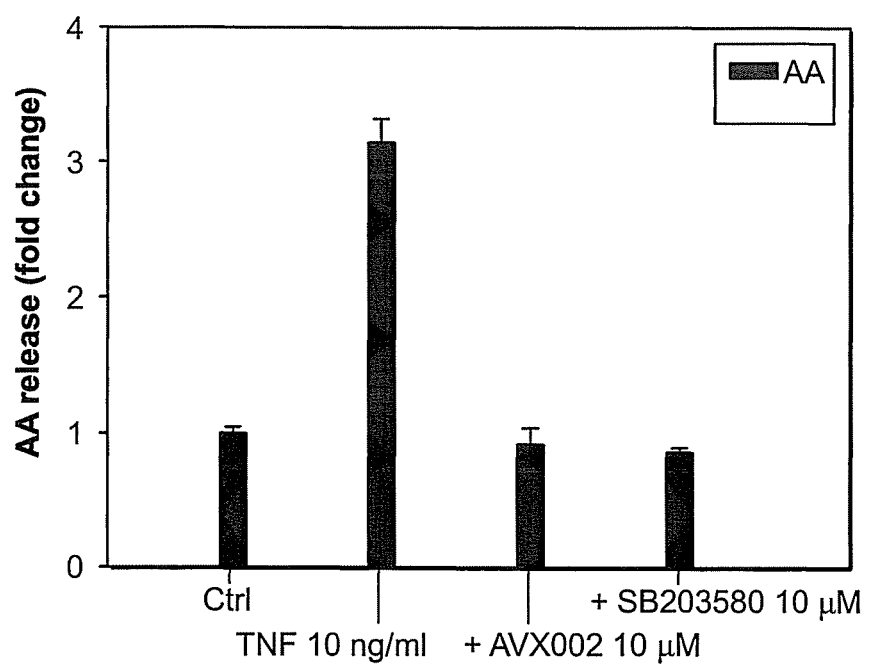
FIG. 1b compares ararchidonic acid release on TNF stimulated SW982 cells.

We evaluted inhibition in SW982 cells by analyzing arachidonic acid (AA) release in response to TNF with or without inhibitor pre-treatment. Compound 2 efficiently reduced the TNF-induced release of AA with an 1050 value of ~1 µM. The inhibitory effect of Compound 2 was compared to that of ATK and SB203580 (FIG. 1b). TNF-induced (10 ng/ml) release of arachidonic acid is efficiently reduced by Compound 2 compared to other relevant inhibitors. Compound 2 normalizes AA-release to basal level, without short-circuiting AA-release all together.

Example 3

Regulation of TNF Induced PGE$_2$ Induction by Compound 1 and Compound 2

Figure 2:
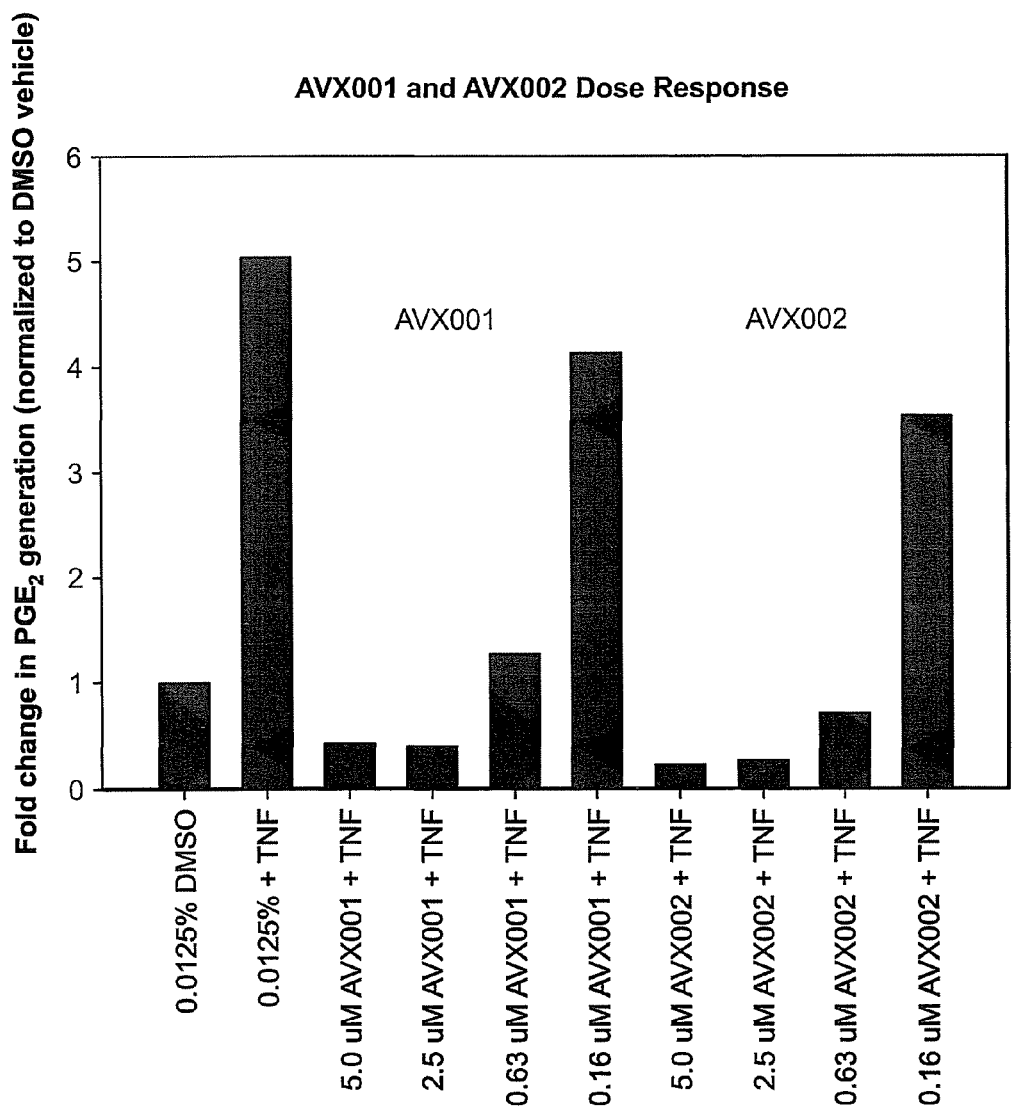
FIG. 2 shows the amount of $PGE_2$ production in SW982 cells after stimulation with TNF for 18 hours. $PGE_2$ production was monitored by ELISA. Those cells receiving treatment underwent reincubation (prior to stimulation) with either Compound 1 (AVX001) or Compound 2 (AVX002) for 2 hours.
Figure 3A:
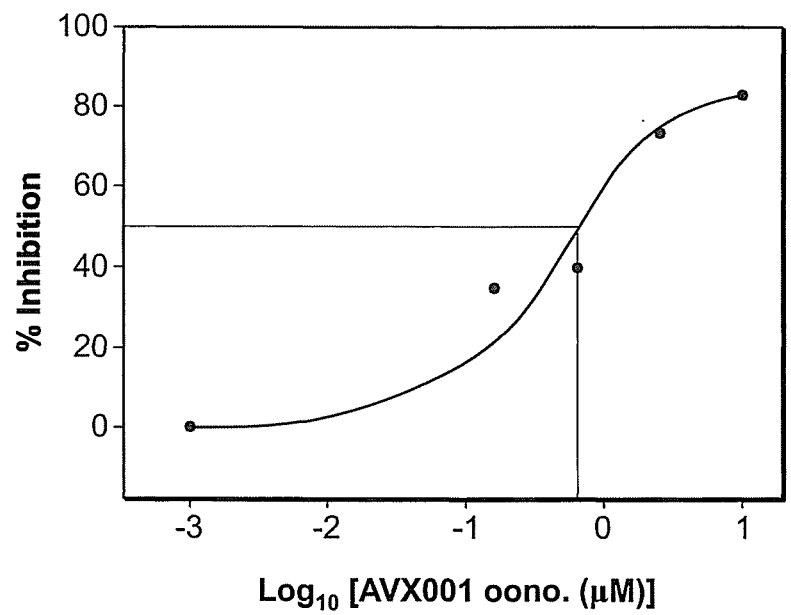
FIGS. 3A and 3B show the determination of $IC_{50}$ values for Compound 1 and Compound 2 inhibition of TNF induced $PGE_2$ production in SW982 cells. 100% inhibition corresponds to the $PGE_2$ level induced with TNFα in combination with ethanol after incubation for 24 hours.
Figure 3B:
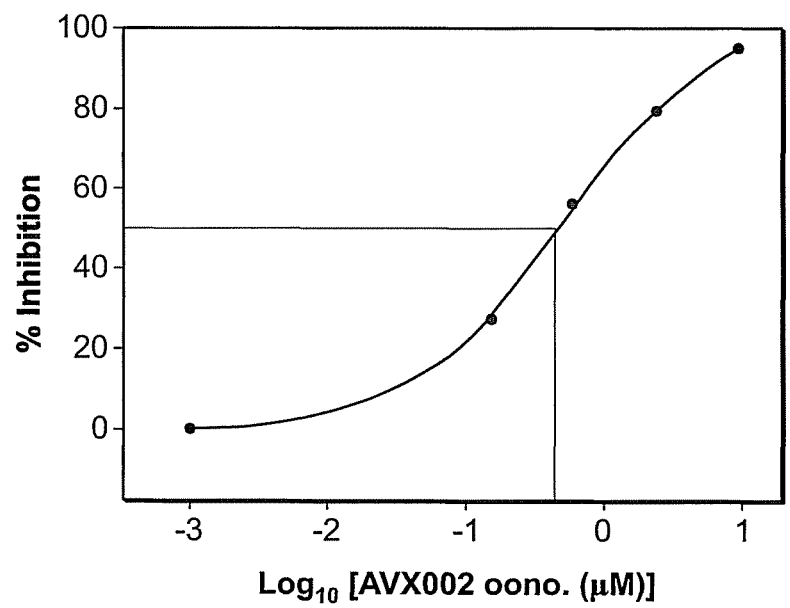

SW982 cells were stimulated with TNF for various lengths ranging from 12-48 hours. TNF stimulation induces increased PGE$_2$ production, which is clearly shown in FIG. 2. However, surprisingly, this PGE$_2$ production can be dose dependently inhibited by Compound 1 and Compound 2 (>100% inhibition at 2.5 µM). FIG. 3 shows the calculation of IC$_{50}$ values of ~630 nM and ~430 nM respectively for Compound 1 and Compound 2 inhibition of TNF induced PGE$_2$ production.

PGE$_2$ is an important regulator of the inflammatory process in the RA joint. The data in FIGS. 2 and 3 indicate that the compounds of the invention would be suitable for use in treating RA.

We found that Compound 2 is just as efficient as the commercial inhibitor ATK in reducing the production of PGE$_2$ by SW982 cells in response to TNF stimulation. Both inhibitors reduced PGE$_2$ production to basal levels in contrast to SB203580 which depleted PGE$_2$ levels to below basal release. This inhibitory effect of SB203580 is consistent with previous reports.

Example 4

Inhibition of TNF-Induced IL8 Production by Compound 1

Figure 4:
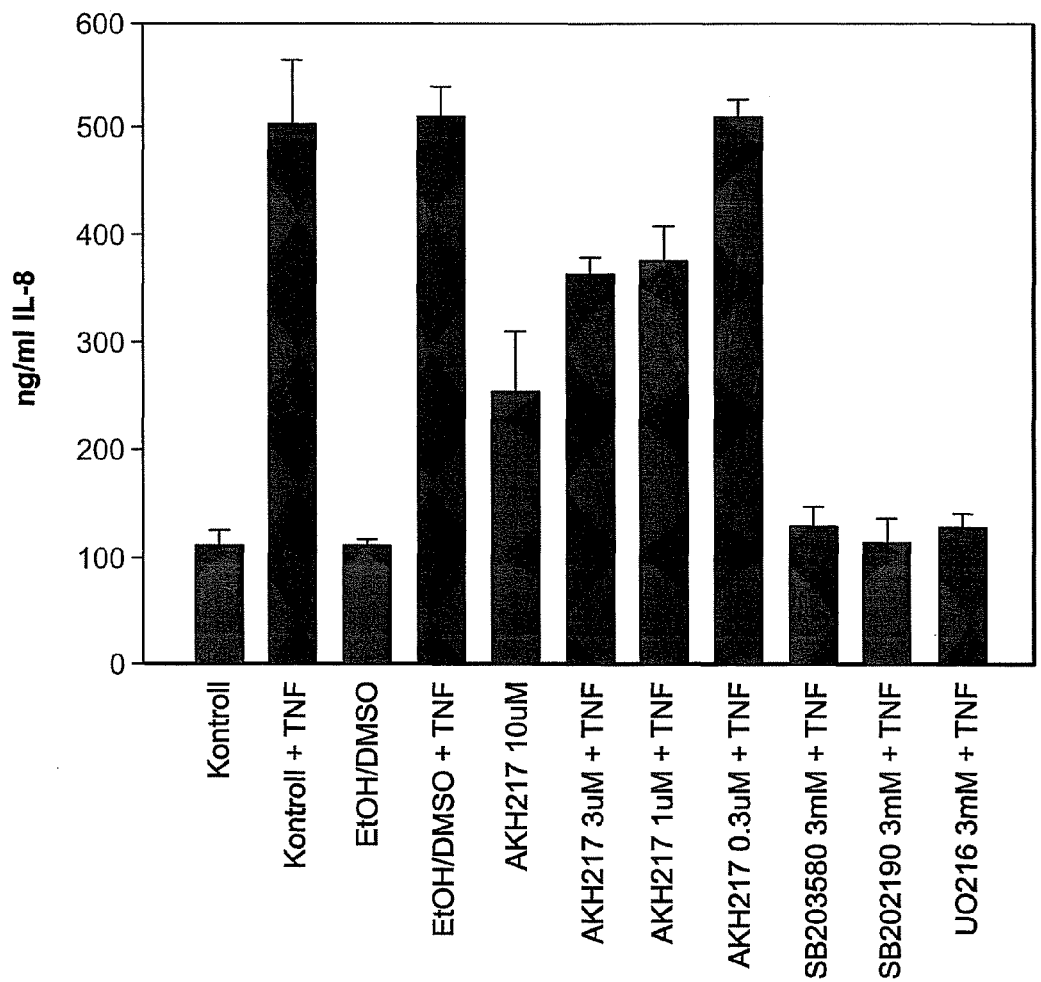
FIG. 4 shows the dose dependent inhibition of IL8 production with Compound 1 (AKH217). SW982 cells were preincubated for 2 hours with inhibitors, and stimulated for 12 hours with TNF. The control contained 0.05% ethanol and 0.05% DMSO, the same quantities of solvent as in the highest concentration of inhibitors. IL8 production was measured by ELISA.

Synoviocyte proinflammatory mediators, such as IL8, are important regulators of the inflammatory response in the joint, both on chondrocytes, cartilage and in autocrine manner on synoviocytes. FIG. 4 shows IL8 levels in SW982 cell lines stimulated with TNF (FIG. 4) monitored by ELISA. FIG. 4 shows that Compound 1 displays dose dependent inhibition of IL8 production.

Example 5

Regulation of TNF Induced Activation of NF-kB Regulated Transcription Factor ESE-1 by the Compounds of the Invention ESE-1 belongs to the ets transcription factor family, which is defined by a highly conserved DNA binding domain of ca 85 amino acids called the ets-domain. Ets transcription factors have been shown to regulate genes involved in diverse functions, including cell proliferation and differentiation, cell cycle progression, angiogensis, and malignant transformation. ESE-1 has been found to be highly upregulated in RA synovial tissue. The ESE-1 promoter contains binding sites for a number of cofactors, though NF-kB is believed to be the principal regulator.

Figure 5:
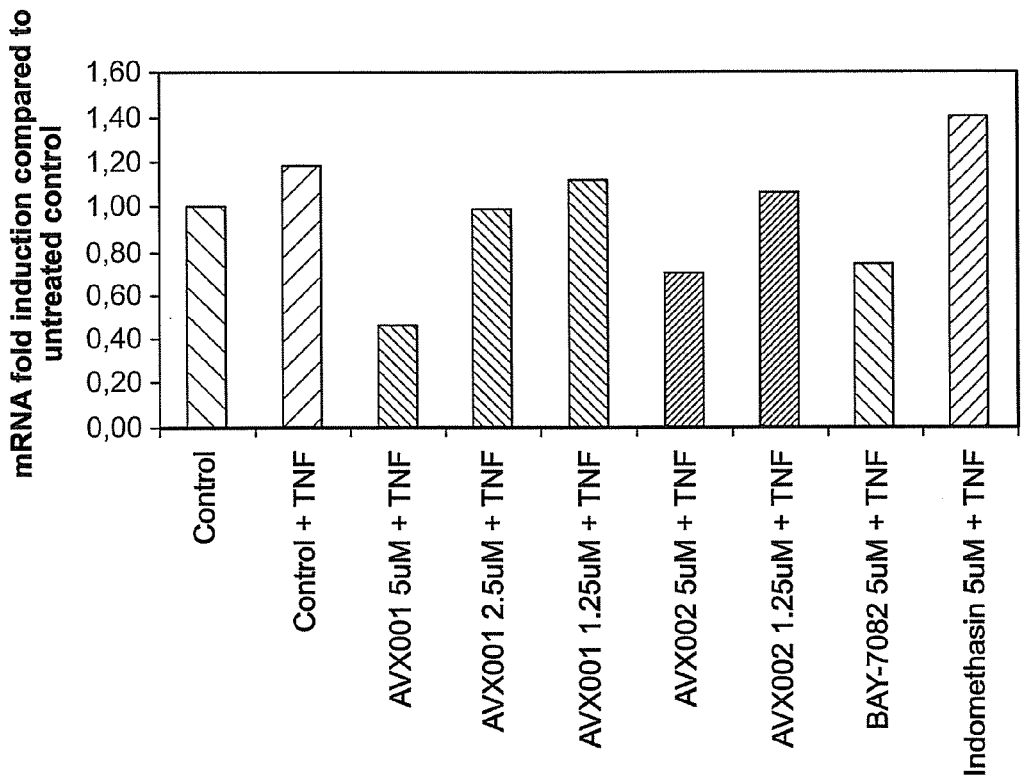
FIG. 5 shows the change in ESE-1 mRNA expression in three days postconfluent SW982 cells. The cells were starved in 0% FCS-DMEM overnight before experimental treatment consisting of 2 hours preincubation of inhibitors followed by 6 hours stimulation with 10 ng/ml TNF

FIG. 5 shows that TNF-induced ESE-1 activation is regulated by Compound 1 and Compound 2 in a dose dependent manner. As a control, the NF-kB inhibitor BAY-7082 is included.

The data in FIG. 5 show that Compound 1 and Compound 2 display similar, if not better, regulation of ESE-1 expression than the known NF-kB inhibitor BAY-7082. In contrast, the known NSAID indomethasin shows poorer regulation of TNF induced ESE-1 expression than the control.

Example 6

Compound 2 Affects the Transcriptional Regulation of Many Genes Associated to Inflammation and Joint Destruction The expression of COX2, MMP and IL-8, both known to be central in inflammation and/or joint destruction was evaluated by quantiative RT-PCR. SW 982 cells were seeded at a density of $0.1 \times 10^6$ cells/well in a 6-well format and then serum-starved after reaching 2-days post confluency. Cells were preincubated with or without inhibitors for 2 hrs prior to treatment in absence or presence of TNF for 24 hrs. The fold-difference in expression of target inflammatory genes relative to an endogenous control (GAPDH) was determined using $\Delta\Delta Ct$ method ($\Delta\Delta Ct = Ct_{target} - Ct_{GAPDHt})_{treated} - (Ct_{target} - Ct_{GAPDH})_{untreated}$. Mean±SD of 3 separate experiments.

Figure 6:
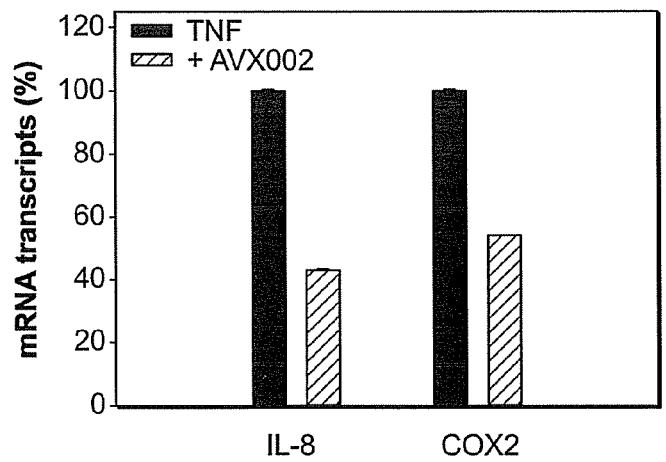
FIG. 6 shows the effects of Compound 2 on the expression of COX2 and IL-8 in TNF stimulated SW982 cells.

After 24 h TNF stimulation, the messages for IL-8, MMP and COX2 increased by 90-fold, 120-fold and 11-fold, respectively (table 2 and FIG. 6). The upregulation was reduced when the cells were pretreated with the Compound 2 inhibitor which on average inhibited the induction of IL-8 and COX2 message by ~53%, ~58% (MMP3) and ~42%, respectively.

TABLE 2

Changes in gene expression in response to TNF and Compound 2. Average fold induction (n = 3)

| Transcript | TNF | Compound 2/ TNF | % Inhibition |
|---|---|---|---|
| IL-8 | 90.92 +/− 37.33 | 39.21 +/− 10.76 | 53.49 |
| COX2 | 11.03 +/− 7.55 | 5.40 +/− 4.32 | 42.22 |

Example 7

Prostaglandin E2 Synthesis is Drastically Reduced by Compound 2

As Compound 2 efficiently reduced the release of AA, we next investigated if inhibition was also reflected in the subsequent conversion of AA to PGE2, an important regulator of both inflammatory and destructive processes in the joint.

We found that the inhibitors of the invention are efficient in reducing the production of PGE2. Results are presented in Table 3.

TABLE 3

| | Mean PGE2 | STDDEV | Fold change 1 | Fold change 2 | Mean | Std-Deviation | % Inhibition |
|---|---|---|---|---|---|---|---|
| Ctrl | 210.2 | 98.8 | 1.00 | 1.00 | 1.00 | 0.0 | |
| TNF | 1888.8 | 52.0 | 13.72 | 6.61 | 10.17 | 5.0 | 0 |
| 10 uM Compound 2 + TNF | 147.5 | 56.7 | 1.34 | 0.38 | 0.86 | 0.7 | 103.7 |
| 5 uM Compound 2 + TNF | 87.5 | 3.5 | 0.64 | 0.30 | 0.47 | 0.2 | 107.3 |
| 10 uM SB + TNF | 25.6 | 1.2 | 0.18 | 0.09 | 0.14 | 0.1 | 111.0 |

The evidence presented in the examples above clearly shows that the inhibitors of the invention have therapeutic potential in the treatment of RA.

Example 8

Compound 2 is More Effective than ENBREL® (Etanercept) in Reducing an Arthritis Index (AI) in a Mouse Model of Collagen-Induced Arthritis (CIA)

Figure 7:
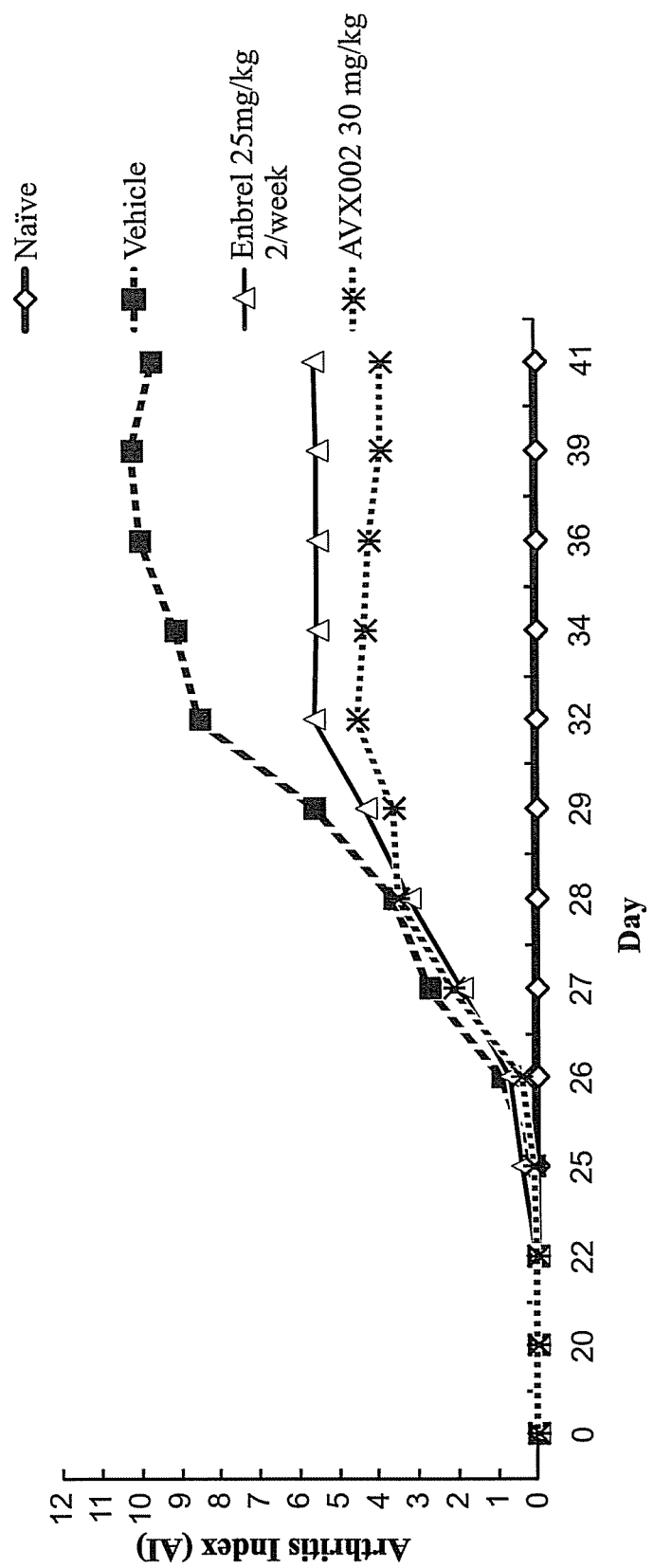
FIG. 7 shows the effects of Compound 2 in a study of therapeutic efficacy in a mouse model of collagen-induced arthritis.

CIA was induced in male DBA/1 mice (except naive group) by immunization with 0.1 mL emulsion containing an equal volume of bovine collagen solution (2 mg/mL) and Freund's Complete Adjuvant antigen solution at the tail base. The first injection was given on Day 0 and the second injection as booster was given on Day 21. Treatment was started on Day 28 and continued for 14 days. Data are presented in FIG. 7.

The invention claimed is:

1. A method of treating rheumatoid arthritis comprising administering to an animal in need thereof an effective amount of a pharmaceutical compound of the following formula:
   wherein X is

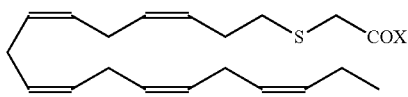

or a salt thereof.

2. The method of claim 1, wherein said animal is a mammal.
3. The method of claim 1, wherein said animal is a human.
4. The method of claim 1 wherein the pharmaceutical compound is administered orally.
5. The method of claim 1 wherein the pharmaceutical compound is administered topically.
6. A method of treating rheumatoid arthritis comprising administering orally or topically to an animal suffering from rheumatoid arthritis an effective amount of a pharmaceutical compound of the formula:
   wherein X is

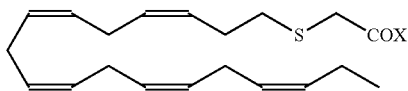

7. The method of claim 6 wherein the pharmaceutical compound is administered orally.

8. The method of claim 6 wherein the pharmaceutical compound is administered topically.

\* \* \* \* \*